United States Patent

Cassidy et al.

Patent Number: 5,314,542
Date of Patent: May 24, 1994

[54] NITROSOMONAS PRESERVATION AND REACTIVATION FOR AQUARIA

[75] Inventors: Edward J. Cassidy, Stuart; Ronald D. Jones, Sunrise, both of Fla.

[73] Assignee: Precision Aquarium Testing, Inc., Stuart, Fla.

[21] Appl. No.: 103,453

[22] Filed: Aug. 6, 1993

[51] Int. Cl.$^5$ .......................... A01K 61/00; C12N 1/20; C12N 1/38; C12N 9/06
[52] U.S. Cl. .................................... 119/231; 210/903; 435/252.1; 435/253.6; 435/244; 435/191
[58] Field of Search ................ 119/3, 4, 5, 200, 231, 119/264, 215; 210/610, 611, 903; 435/244, 191, 253.6, 252.1

[56] References Cited

U.S. PATENT DOCUMENTS

| | | | |
|---|---|---|---|
| 4,218,540 | 8/1980 | Ackerman | 435/243 |
| 4,290,891 | 9/1981 | Ackerman | 210/611 |
| 4,874,707 | 10/1989 | Bock | 435/253.6 |
| 5,211,872 | 5/1993 | Goldstein et al. | 252/180 |

*Primary Examiner*—Thomas Price

[57] ABSTRACT

A culture of Nitrosomonas packaged in a manner to induce a metabolic state of dormancy under conditions favorable for survival of up to at least one year at room temperature: with a method for its rapid reactivation to complete metabolic activity within about 72 hours: for its subsequent addition into aquaria to immediately begin the oxidation and prevention of harmful ammonia accumulation.

1 Claim, No Drawings

NITROSOMONAS PRESERVATION AND REACTIVATION FOR AQUARIA

BACKGROUND OF THE INVENTION

1. Field of the Invention

This invention relates to aquarium maintenance, specifically an active culture of Nitrosomonas for oxidizing ammonia.

2. Discussion of Prior Art

Nitrosomonas is a genus of bacteria in aquaria which oxidize ammonia. A toxic waste product of animals, ammonia accumulates causing injury or death to aquarium inhabitants.

When fish or other animals are added to an aquarium, a small number of Nitrosomonas are carried with them and introduced into the aquarium. As aquarium animals produce ammonia, the Nitrosomonas begin to oxidize it into nitrite.

Ammonia is produced faster than the rate at which the small number of Nitrosomonas can oxidize it. Ammonia levels rise to toxic levels, killing or injuring aquarium inhabitants until a sufficiently large population of Nitrosomonas develops to keep ammonia levels at or near zero.

Unlike many bacterial species, Nitrosomonas do not have the ability to produce spores. Many bacterial species are capable of producing dormant spores which are resistant to adverse environmental conditions.

When starved of ammonia, under certain conditions, the vegetative Nitrosomonas cell is capable of becoming dormant and surviving in this state without ammonia, its only food and source of energy, for years. While dormant, however, the cell is not resistant to adverse environmental conditions. While dormant the Nitrosomonas cell is much more sensitive to adverse conditions such as chemical insults and exposure to light.

Nitrosomonas are relatively slow to reproduce compared to most other bacterial species. To accelerate the establishment of the needed population of Nitrosomonas in an aquarium, many commercial products claiming to contain live Nitrosomonas are available. It is claimed that the addition of these products will prevent toxic ammonia accumulation.

Heretofore, these products suffer from a number of disadvantages:

(a) If the product is a dried or freeze dried culture little or none of the Nitrosomonas cells survive. This type of processing kills all or almost all Nitrosomonas cells. Adding dead cells increases the amount of organic material available for decomposition thereby increasing the amount of ammonia produced. Adding only a few live cells which might survive this type of processing does not have an appreciable effect on reducing ammonia accumulation.

(b) If a liquid culture of Nitrosomonas is packaged in a closed container with an ammonia (i.e. energy) supply present cells may die as a result of oxygen starvation.

(c) If a liquid culture of Nitrosomonas is packaged in a closed container with other species of bacteria present, particularly anaerobic varieties, Nitrosomonas cells will die. Death results from the toxic effects of the waste products, such as hydrogen sulfide, produced by other species of bacteria.

(d) If a liquid culture of Nitrosomonas remains suspended in its own culturing media cells will die as a result of exposure to its own waste products.

(e) If a liquid culture of Nitrosomonas is not maintained under aseptic conditions, cells can die as the result of the waste products of other organisms, the action of organisms which can utilize Nitrosomonas as a food, and the action of organisms which can use Nitrosomonas as a host.

(f) Most of the waste products covered in (c) through (e) are also toxic to other aquarium inhabitants. The addition of these cultures to an aquarium can result in the addition of toxic chemicals causing injury or death to aquarium inhabitants.

(g) If a liquid culture as described in (b) through (e) above, is kept under refrigeration, the Nitrosomonas cells can remain alive for a limited time. The limited shelf and high cost for maintaining temperature control has restricted the use of such products.

(h) Any Nitrosomonas cells which survive the packaging procedures described in (a) through (e) and (g), above, will be in a state of metabolic dormancy. When added to an aquarium system, dormant cells require several days before metabolic activity and the ability to oxidize ammonia returns, assuming ammonia is present. During this "lag" period, ammonia levels accumulate to toxic levels killing or injuring aquarium inhabitants.

OBJECTIVES AND ADVANTAGES

Accordingly, the several objects and advantages of our invention are:

(a) To provide a culture consisting of live Nitrosomonas.

(b) To provide such a culture with a reasonable shelf life (i.e. one year).

(c) To provide such a culture with sufficient numbers of cells to prevent or sufficiently alleviate ammonia accumulation.

(d) To provide such a culture that survives when stored at room temperature.

(e) To provide such a culture along with a mechanism allowing for the rapid reactivation of dormant cells to prevent or significantly alleviate ammonia accumulation.

(f) To provide a culture that does not add toxic chemicals to the aquarium.

Further objects and advantages are to provide a culture of live Nitrosomonas which can be used easily and conveniently to prevent ammonia accumulation in aquaria, thereby preventing or reducing injury to aquaria inhabitants, which is simple to use and inexpensive to manufacture. Still further objects and advantages will become apparent from a consideration of the ensuing description.

DESCRIPTION

A starting culture of a suitable Nitrosomonas sp. must first be identified and then obtained for any particular aquarium type application. For tropical marine aquariums, a strain isolated from the sea is suitable. For freshwater aquarium use, a freshwater isolate, such as Nitrosomonas, is needed. Both of these strains are readily available from the American Type Culture Collection, VA.

Such starting cultures are then used to produce the quantities of cells needed, in accordance to the prior art procedures published by Jones (Jones, R. D., and M. A. Hood. 1980. The effects of temperature, pH, salinity and inorganic nitrogen on the rate of ammonium oxidation by nitrifiers isolated from wetland environments. Microbial Ecol. 339-347.).

Exhausted culturing media, with the maximum obtainable cell concentration of is then collected and further processed for preservation under aseptic conditions.

Collected media is then concentrated to approximately one twenty-fifth (1/25) its volume. Concentration can be achieved using centrifugation, filtration or other means.

Concentrate is then resuspended in sterile water of suitable salinity back to its original volume and packaged in sterile opaque containers. The majority of these resuspended cells will begin to enter a metabolic state of inactivity (dormancy), but will remain viable for at least one year.

The preserved cells can at any time be returned to their metabolically active state by adding ammonium chloride (or other suitable salt such as ammonium sulfate) to the opaque container to bring the ammonia concentration to about 200 ppm.

Experimentation has demonstrated that this is the ideal concentration for bringing dormant Nitrosomonas back to a fully metabolically active state in the shortest period of time.

In addition to ammonia a suitable buffer, such as calcium carbonate, is added to prevent an adverse drop in pH resulting from the oxidation of ammonia.

The opaque Container is then left uncapped in a dark place for about 72 hours.

From the above description, a number of advantages Of our process for Nitrosomonas preservation and reactivation for aquaria use become evident:

(a) Concentrating and then resuspended the Nitrosomonas in sterile water provides an environment free from the toxic waste products produced during culturing increasing survival rates during storage.

(b) Concentrating and then resuspending the Nitrosomonas in sterile water provides an environment free from potentially harmful species of other organisms increasing survival rates during storage.

(c) Concentrating and then resuspending the Nitrosomonas in sterile water provides an environment free from most ammonia, quickly inducing a state of dormancy, thereby minimizing the adverse effects of oxygen depletion and increasing survival rates during storage.

(d) Concentrating and then resuspending the Nitrosomonas in sterile water removes most of the toxic waste produced during culturing prior to its addition into the aquarium.

(e) The process provides a culture which can be kept at at room temperature and still remain viable.

(f) The process provides a culture which will remain viable for at least one year.

(g) The process provides a culture which will contain a sufficient number of viable Nitrosomonas to prevent or alleviate ammonia accumulation.

(h) The process provides a mechanism for insuring the rapid reactivation of the dormant Nitrosomonas cells so that they are ready to immediately begin ammonia oxidation as soon as it is made available.

(i) The mechanism for reactivation insures that ammonia will be oxidized as soon as it is produced within the aquarium environment before it accumulates to levels which are toxic to aquarium inhabitants.

(j) The mechanism for reactivation exposes the dormant Nitrosomonas to ammonia levels in the area of 200 ppm. This is the ideal concentration for bringing the dormant cells back to an active metabolic state in the shortest period of time possible. This level is tens of times higher than what would naturally occur in an aquarium environment.

(k) The mechanism for reactivation insures that organisms will receive the required amount of dissolved oxygen as metabolic activity returns.

(l) The mechanism for reactivation insures that the organism is not exposed to the harmful effects of light.

(m) The mechanism for reactivation insures that the organism is not exposed to harmful pH changes.

OPERATION OF INVENTION

The preferred embodiment of this invention involves the use of an opaque bottle containing a suitable volume of resuspended dormant Nitrosomonas cells and several accessory chemicals. For example, a one ounce opaque vial will contain sufficient cells to successfully establish most size aquariums, commonly used by hobbyist aquarists.

After removing the vials cap, sufficient ammonia is added to bring the one ounce of liquid culture to about a 200 ppm concentration. Serveral drops of a 25% ammonium chloride solution can be used.

A suitable buffer, such as a 600 mg tablet of calcium carbonate is then added.

The uncapped vial is then placed in a dark location, such as a cupboard, for about 72 hours to allow sufficient time for the dormant Nitrosomonas cells to return to a metabolically active state.

After about 72 hours the culture and some ammonia producing organisms, such as fish, are then added to the tank.

For user convenience, additional accessory chemicals, such as dechlorinators and trace elements can also be included as separate additives for addition to the aquarium.

Conclusion, Ramifications, and Scope of Invention

Thus the reader will see that the Nitrosomonas culture and the method described in the invention for its reactivation, provides a highly reliable, easy to use, and convenient product for introducing metabolically active ammonia oxidizing bacteria into an aquarium to prevent ammonia accumulation thereby preventing or reducing injury to aquaria inhabitants.

While our above description contains many specificities, these should not be construed as limitations on the scope of the invention, but rather as an exemplification of one preferred embodiment thereof. Many other variations are possible. For example, the culture and reactivation of other ammonia oxidizing bacteria genera could be used rather than Nitrosomonas. In addition, the amount of dormant cells packaged and reactivated can be adjusted to compensate for different sizes in the aquaria treated. Accordingly, the scope of the invention should be determined not by the embodiment(s) illustrated, but by the appended claims and their legal equivalents.

We claim:

1. A method for reactivating a metabolic activity of liquid culture of dormant ammonia oxidizing bacteria prior to their addition into an aquarium, comprising the steps of:
   a. increasing a concentration of ammonia in said liquid culture to about 200 ppm, and
   b. waiting about 72 hours to restore the metabolic activity of said dormant ammonia oxidizing bacteria before adding said culture into said aquarium.

* * * * *